United States Patent
Harper

(10) Patent No.: US 10,515,629 B2
(45) Date of Patent: Dec. 24, 2019

(54) SYSTEM AND METHOD FOR ACTIVATION OF VOICE INTERACTIVE SERVICES BASED ON USER STATE

(71) Applicant: Sonde Health, Inc., Boston, MA (US)

(72) Inventor: James D Harper, Jamaica Plain, MA (US)

( * ) Notice: Subject to any disclaimer, the term of this patent is extended or adjusted under 35 U.S.C. 154(b) by 0 days.

(21) Appl. No.: 15/484,610

(22) Filed: Apr. 11, 2017

(65) Prior Publication Data

US 2018/0254041 A1   Sep. 6, 2018

Related U.S. Application Data

(60) Provisional application No. 62/320,699, filed on Apr. 11, 2016.

(51) Int. Cl.
| | | |
|---|---|---|
| G10L 15/18 | (2013.01) | |
| G10L 25/51 | (2013.01) | |
| G06Q 50/22 | (2018.01) | |
| G06Q 10/10 | (2012.01) | |
| G10L 17/26 | (2013.01) | |
| G10L 15/08 | (2006.01) | |

(52) U.S. Cl.
CPC .......... G10L 15/1815 (2013.01); G10L 25/51 (2013.01); *G06Q 10/1095* (2013.01); *G06Q 50/22* (2013.01); *G10L 17/26* (2013.01); *G10L 2015/088* (2013.01)

(58) Field of Classification Search
CPC ....................................................... G10L 17/26
See application file for complete search history.

(56) References Cited

U.S. PATENT DOCUMENTS

| | | | |
|---|---|---|---|
| 2012/0265024 A1* | 10/2012 | Shrivastav | A61B 5/40 600/300 |
| 2013/0159229 A1* | 6/2013 | Modha | G06N 3/08 706/16 |
| 2017/0249437 A1* | 8/2017 | Jain | G16H 50/20 |

FOREIGN PATENT DOCUMENTS

EP   2712454 A1 *  4/2014 ............. A61B 5/117

\* cited by examiner

*Primary Examiner* — Feng-Tzer Tzeng
(74) *Attorney, Agent, or Firm* — Ashok Tankha

(57) ABSTRACT

The present invention provides a system for activating personal assistance services. The system includes an audio data collector adapted to collect a sample of speech, a processing module, and a service activator couple to an output device. The processing module further includes an audio feature extractor that extracts a plurality of acoustic features from the sample of speech, and a classification unit that classifies a status of a user from the plurality of acoustic features. The Service activator activates a personal assistance service according to the status of the user classified by the classification unit.

21 Claims, 9 Drawing Sheets

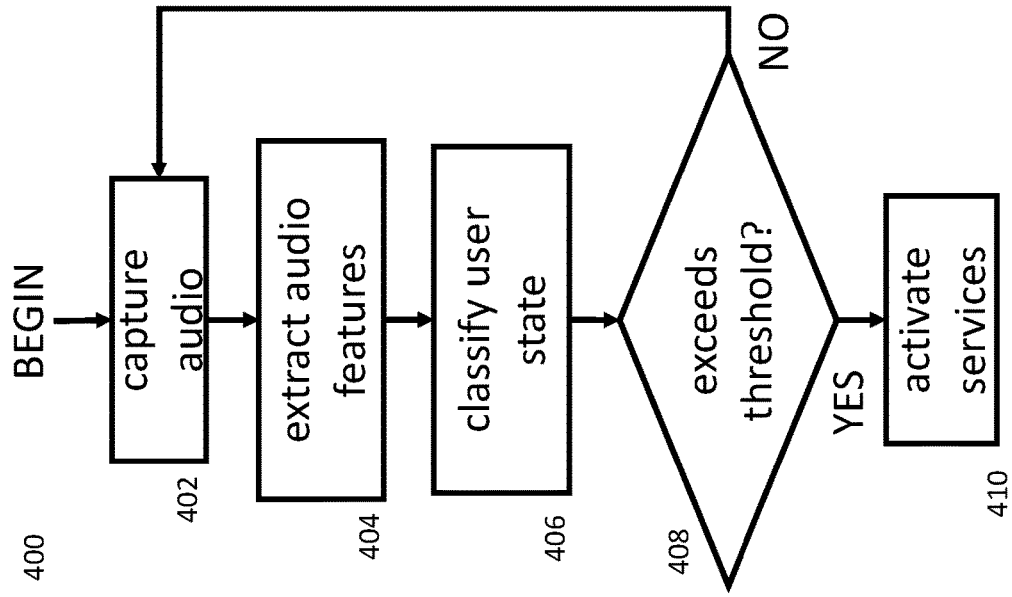

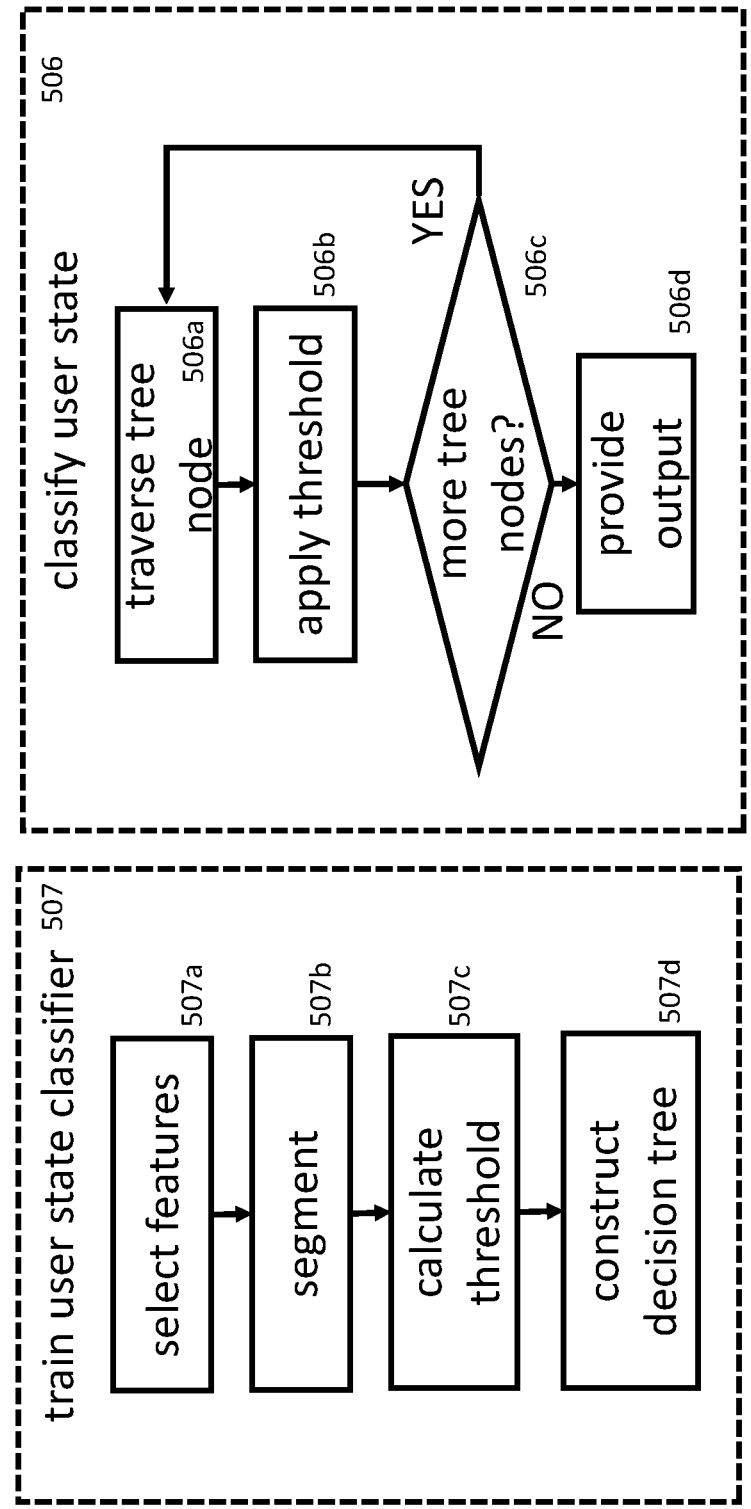

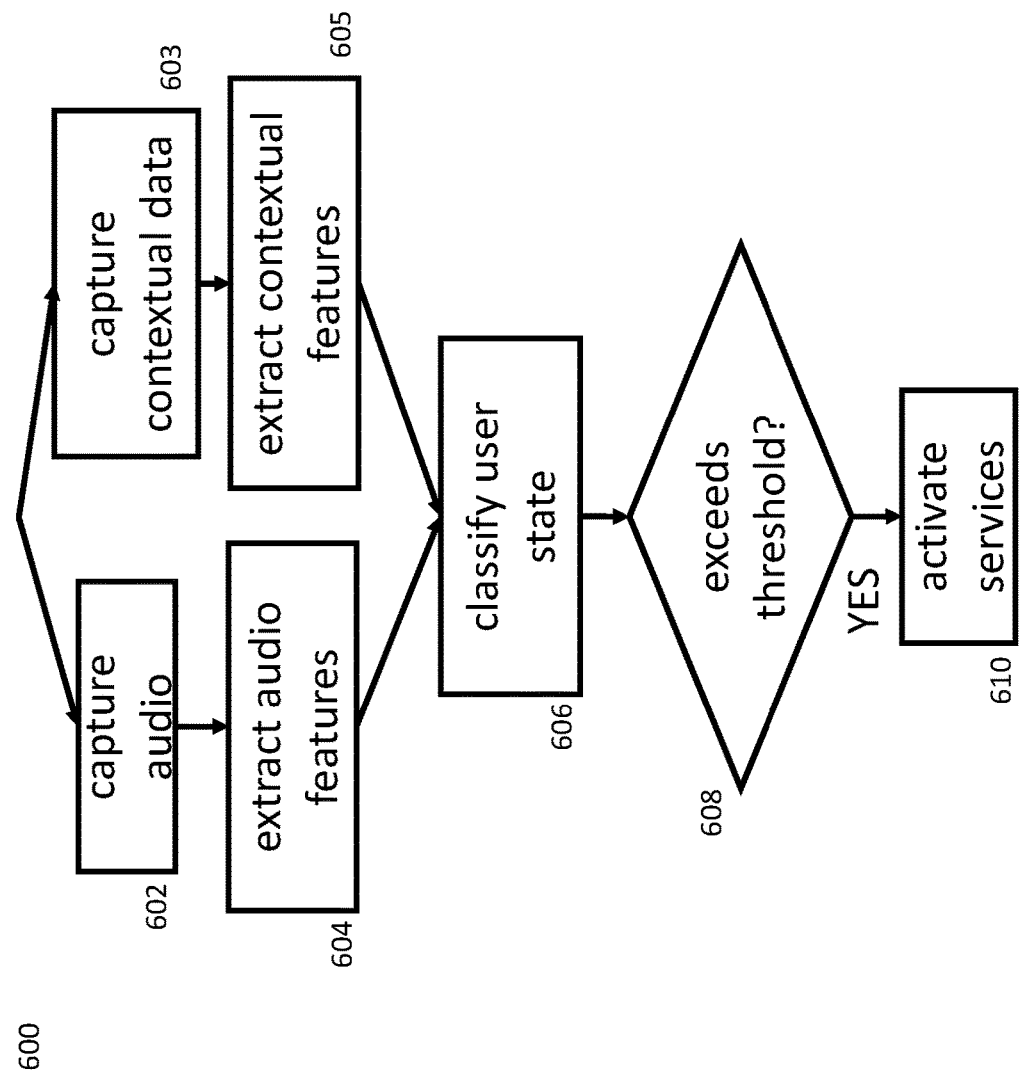

US 10,515,629 B2

SYSTEM AND METHOD FOR ACTIVATION OF VOICE INTERACTIVE SERVICES BASED ON USER STATE

CROSS REFERENCE TO RELATED APPLICATIONS

This application claims the benefit of the filing date of U.S. Provisional Patent Application 62/320,699, entitled "VOICE INTERACTIVE DEVICE OPERATION BASED ON NON-LINGUISTIC CUES" to James D. Harper, which was filed on Apr. 11, 2016, the disclosure of which is hereby incorporated entirely herein by reference.

TECHNICAL FIELD

The present invention relates to intelligent assistants. More specifically, embodiments of the present invention relate to intelligent automated assistants that can be improved by detecting and processing user state information represented in the non-linguistic or paralinguistic content of their voice interactions with the system.

BACKGROUND

Today's electronic devices are able to access a large, growing, and diverse quantity of functions, services, and information, both via the Internet and from other sources. Functionality for such devices is increasing rapidly, as many consumer devices, smartphones, tablet computers, and the like, are able to run software applications to perform various tasks and provide different types of information. Increasingly, these devices have become the hub for managing important health data. They run a range of independent health applications and interface with a range of wearable and clinical sensing devices. While these apps and devices can be important tools in systems designed to monitor and improve individual health, each one has different interfaces and interaction needs and schedules that need to be engaged regularly for maximum benefit. Many of these interactions can be burdensome and become overwhelming or frustrating for users in ways that lead to decreased utilization of the tools or lack of awareness when input is needed or helpful information is available.

In particular, individuals who are impaired or disabled in some manner, and/or are elderly, young, unfamiliar with a device, busy, distracted, and/or operating a vehicle may have difficulty interfacing with their electronic devices effectively, and/or engaging online services effectively. Such users are particularly likely to have difficulty with the large number of diverse and inconsistent health functions, applications, and websites that may be available for their use.

Additionally, individuals who consider themselves healthy may be less likely or inclined to initiate use of health monitoring and screening applications or features that could help anticipate and even prevent potential medical problems.

Existing automated assistant systems rely on linguistic cues to recognize key words or phrases to activate the device and link the speaker of the key word or phrase to predefined service domains estimated to be relevant based on the semantic content of speech subsequent to the key word or phrase. For example, the intelligent automated assistant described in Apple's Siri patent U.S. Pat. No. 8,670,979 B2 makes use of linguistic content of human speech to cue services and content provided to a user.

SUMMARY

The present invention provides a system for activating personal assistance services, the system. The system includes an audio data collector adapted to collect a sample of speech, a processing module including an audio feature extractor and a classification unit, and a service activator couple to an output device. The audio feature extractor extracts a plurality of acoustic features from the sample of speech, and the classification unit classifies a status of a user from the plurality of acoustic features. Also, the service activator activates a personal assistance service according to the status of the user classified by the classification unit.

The present invention also provides a method for providing a mental and physical health-context-aware intelligent automated assistant that derives this contextual information from non-linguistic content of speech and other human sounds. The method includes receiving a user-generated sound through an audio data collector, the user-generated sound including a user-generated request, other speech, cough, sneeze, breathing sound, or other sound resulting from a user's activity, classifying a mental or physical health state of the user from a plurality of predetermined health domains, the classifying being performed by a processor and memory storing instructions for execution by the processor, when executed, the stored instructions processes non-linguistic qualities of the audio input, determining, based on a classified user state, an area of service offered by the intelligent automated assistant, and finally, activating a health-related service to the user.

BRIEF DESCRIPTION OF THE DRAWINGS

FIG. 4A-C depicts a method for activating personal assistance services according to an embodiment of the present inventions;

FIG. 5A-C depict a method for classifying a user state according to an embodiment of the present inventions;

FIG. 6 depicts a method for activating personal assistance services based on a classified user status according to another embodiment of the present inventions

DETAILED DESCRIPTION

Figure 1:
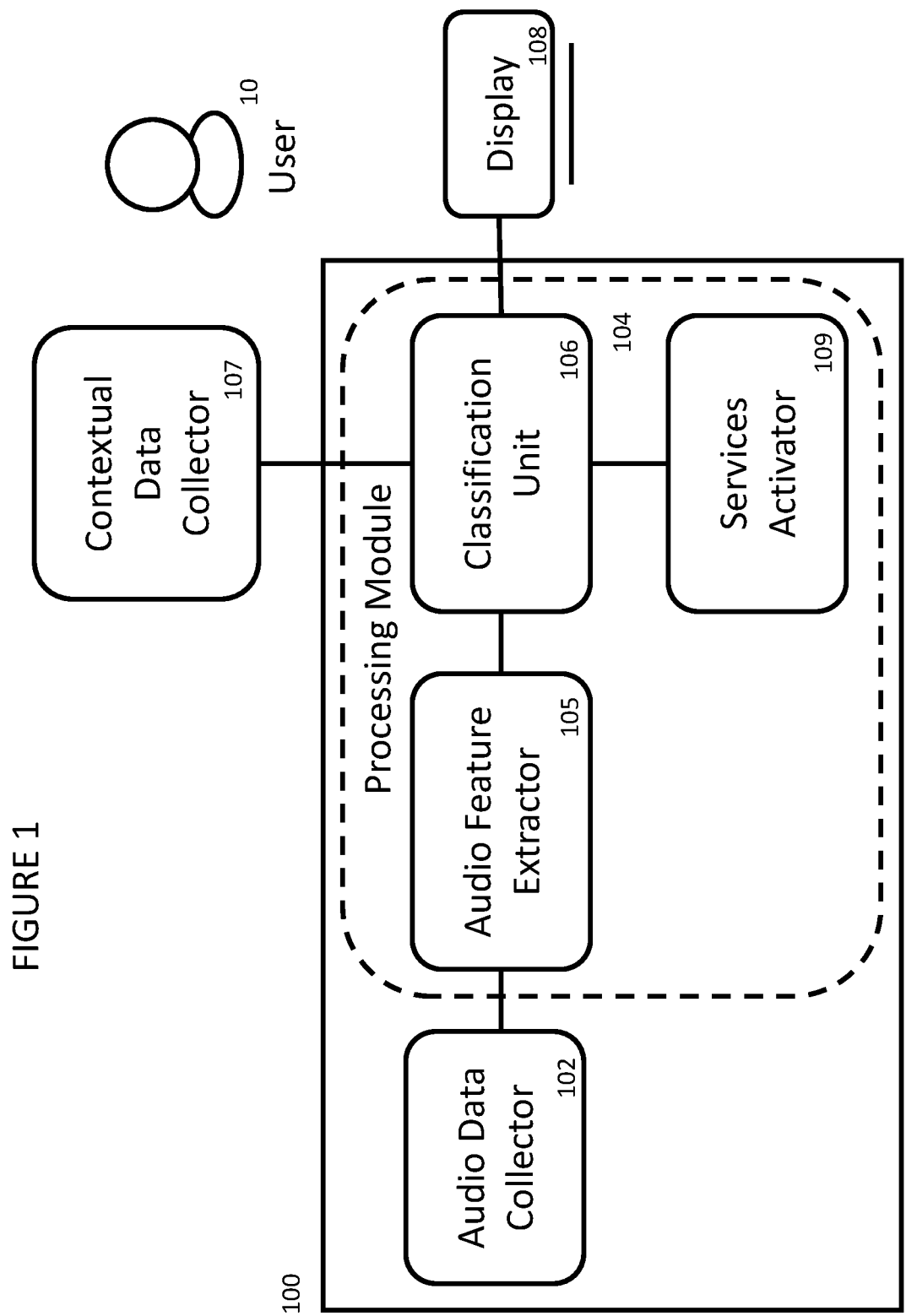
FIG. 1 depicts a system for activating personal assistance services according to an embodiment of the present inventions.

Non-linguistic cues are superior for guiding the activation of digital health related services. Reducing the delay between a change in health status and making accurate information characterizing that change available to patients and the people or services coordinating their health care is a very important pre-requisite for enabling earlier intervention and improved treatment outcomes across a wide range of health conditions. Because user-generated requests represent only a small fraction of user-generated sounds containing potential health information made by an individual near an audio data collector, the potential to monitor all audio produced by an individual not limited by inclusion of a key word or phrase or understandable user request allows significantly increased monitoring frequency and reduced latency for health information. For health applications dependent on detecting and measuring rapidly improving or declining health states like development of novel fast-acting depression therapeutics and detection of neurological conditions like epilepsy and stroke with rapid episodic onset, analysis of user-generated requests would not have sufficient measurement frequency to provide meaningful responses on timeframes relevant to the condition. Importantly, simple solutions where audio data collectors are always on and analyzing linguistic content of incoming user-generated-audio will be impractical in many health monitoring embodiments that rely on battery power or that would benefit from increased levels of user privacy. In these cases having an always-on health activity detection capability that is analogous to voice activity detection capabilities allow analysis and storage of health-related acoustic information that can much more efficiently manage power, computational, and storage resources and does not require full waveform recording or storage of linguistic content that may contain sensitive or private user-content and will have increased amounts of identifying information.

Methods, systems, and computer readable storage medium related to operating an intelligent and context-aware automated assistant are disclosed herein. A user request is received through an interactive voice interface of the intelligent context-aware assistant, the user request including at least an audio or speech input received from a user. One or more candidate mental or physical health domains relevant to the user request are identified from a plurality of predefined health domains, where each predefined domain presents a respective area of service offered by the context-aware intelligent automated assistant, and the identifying is based on respective degrees of match between contextual states of the user estimated from non-linguistic or paralinguistic features of audio or speech and contextual states associated with each predefined domain. Feedback is provided to the user through the conversation interface of the intelligent automated assistant, where the feedback presents a description of the contextual state detected and elicits additional input from the user to further estimate the contextual state, specifies one or more parameters associated with a particular candidate domain relevant to that state, shares information and data about that health state with one or more users or health care providers, and/or schedules appointments or pre-defined services to further diagnose, monitor, or treat the health state.

Activation of existing voice interactive systems is achieved either through physical manipulation of the device (e.g. a button push) or via passive pattern-matching analysis of voice to detect certain words or phrases that a system is pre-configured or trained to recognize as activation commands. Such keyword or pass-phrase controlled systems that use only linguistic content for control require significant effort to be retrained for different languages, and produce a relatively unnatural and limited set of interaction possibilities that respond poorly to changing context. The use of non-linguistic vocal features to activate the system can enable a much broader and richer interaction interface and creates the possibility for a range of additional functions for voice interactive devices beyond semantic control and responses.

Activation of a system based on detection of specific affect or mood in the voice of an individual in the room could automatically activate the system and direct it to produce a system response appropriate to the state of the individual, as follows.

If sadness or negative affect is detected, system could take actions including ask if they are feeling down, asking if they would like to talk to a friend or family member, and/or ask whether the user wants to play music that has positive lyrics or a major chord progression, etc. (can initiate the music automatically or can adjust a playlist already in progress to change the emotional valence).

If the user is anxious, the system could detect that state, activate, and play soothing music or select from a pre-determined list of activities designed to engage the user in ways that reduce the ability of the individual to focus on the source of the anxiety.

If an argument is detected the system could detect the conflict and anger in speech among multiple users and activate to initiate a predetermined set of actions in response to that situation (record the time and identity of the participants, determine the topic of the argument and respond in a contextually aware manner, initiate activity of a baby monitor or a recording system based on pre-configured system settings (e.g. for detecting verbal abuse by a childcare worker), etc.

If the system detects confusion, it could activate and ask the user if he or she would like any help.

Embodiments of present invention can further include activation of the system based on the health or physiological state of the user's states relating to Depression, Parkinson's or other diseases. Embodiments of present invention can be integrated with other sensors. To further ensure that the detected state is accurately attributed to a specific individual the present invention can be integrated with biometric identification of one or more individuals who speak near the device via analysis of the same voice sample used to assess speaker state or intent or via inputs from other integrated sensors. Embodiments of the present invention can be directed to detect dementia associated loss of direction, etc.

According to embodiments of the present invention, a service activation system is provided that include two sequential stages. An exemplar first stage includes an audio data collector that collects a voice sample from a user.

An exemplar second stage that includes a processing module that performs three main functions: 1) processes the audio or voice sample to extract features to classify a user state, 2) classifies a user voice sample to a predetermined health or physiological state, and 3) activates a service based on the predetermined health or physiological state.

Conventional methods for analyzing a voice audio sample for user states can be provided to classify a plurality of predetermined user states. For example, states or status in depression, anhedonia and other sub-symptoms of Major Depressive Disorder (MDD) may be detected based on vocal biomarkers described in *Vocal and facial biomarkers of depression based on motor incoordination and timing* (James R. Williamson et al.). Another set of features and classification methods can be found in concurrently pending U.S. patent application Ser. No. 15/464,756, filed on Mar. 21, 2017. As another example, states or status of cognitive impairment may be detected based on vocal biomarkers described in *Cognitive impairment prediction in the elderly based on vocal biomarkers* (Bea Yu et al.).

As another example, states or status of cognitive load may be detected based on vocal biomarkers described in *Vocal biomarkers to discriminate cognitive load in a working memory task.* (Thomas F. Quatieri et al.), and *Cognitive load classification using formant features* (Tet Fei Yap et al.).

As another example, states or status of Alzheimer's disease and dementia may be detected based on vocal biomarkers described in *Automatic speech analysis for the assessment of patients with predementia and Alzheimer's disease* (Konig et al.)

As another example, states or status of Parkinson disease (PD) may be detected based on vocal biomarkers described in *Segment-dependent dynamics in predicting Parkinson's disease* (James R. Williamson et al.)

As another example, states or status of Amyotrophic Lateral Sclerosis disease (ALS) may be detected based on vocal biomarkers described in *Relation of automatically extracted formant trajectories with intelligibility loss and speaking rate decline in Amyotrophic Lateral Sclerosis* (Rachelle L. Horwitz-Martin et al.)

As another example, states or status of Coughing frequency and severity may be detected based on vocal biomarkers described in *An update on measurement and monitoring of cough: what are the important study endpoints* (Arietta Spinou et al.).

As another example, states or status of stress may be detected based on vocal biomarkers described in Vocal indices of stress: a review (Cheryl L. Giddens et al.).

As another example, states or status of TBI and concussion symptoms may be detected based on vocal biomarkers described in *Voice and ocular dynamics in classifying cognitive change with preclinical mTBI* (Brian Helfer et al.).

As another example, states or status of Chronic Obstructive Pulmonary Disease (COPD) may be detected based on vocal biomarkers described in *Voice Analysis in individuals with chronic obstructive pulmonary disease* (Anuradha Shastry et al.).

As another example, states or status of user emotion and affect may be detected based on acoustic features described in *Recognising Realistic Emotions and Affect in Speech: State of the Art and Lessons Learnt from the First Challenge* (Bjorn Schuller et al.), and *Long term suboxone emotional reactivity as measured by automatic detection in speech* (Edward Hill et al.) Similarly, states or status of confusion, agitation, sleepiness, anxiety, breathlessness, respiration rate, fluid retention, congestive heart disease, hypoglycemia, hypertension or hypotension, asthma, respiratory viral infection, influenza infection, Multiple Sclerosis (MS), Schizophrenia may be detected.

As shown in FIG. 1, an embodiment of the present invention provides a system 100 for classifying a state or a status of a user. The system 100 includes an audio data collector 102 adapted to collect a sample of speech, a processing module 104 including an audio feature extractor 105 and a classification unit 106, and a service activator. The audio feature extractor 105 extracts a plurality of acoustic features from the sample of speech, and the classification unit 106 classifies a user state or status from the plurality of acoustic features. From the classified user state or status, the service activator activates a service for the user As shown in FIG. 1, the system 100 can further couple with a contextual data collector 107 and a display 108 to collect additional contextual health data from user 10. The performance of system 100 can be furthermore improved by the contextual data such as those activity measurements obtained from accelerometers, light sensors, screen use and interaction data, and phone call, messaging, or data use.

Embodiments of the present invention provides several advantages over existing voice interactive digital assistants. For example, the use of non-linguistic vocal features to activate the system can enable a much broader and richer interaction interface and creates the possibility for a range of additional functions for voice interactive devices beyond semantic control and responses.

Figure 2:
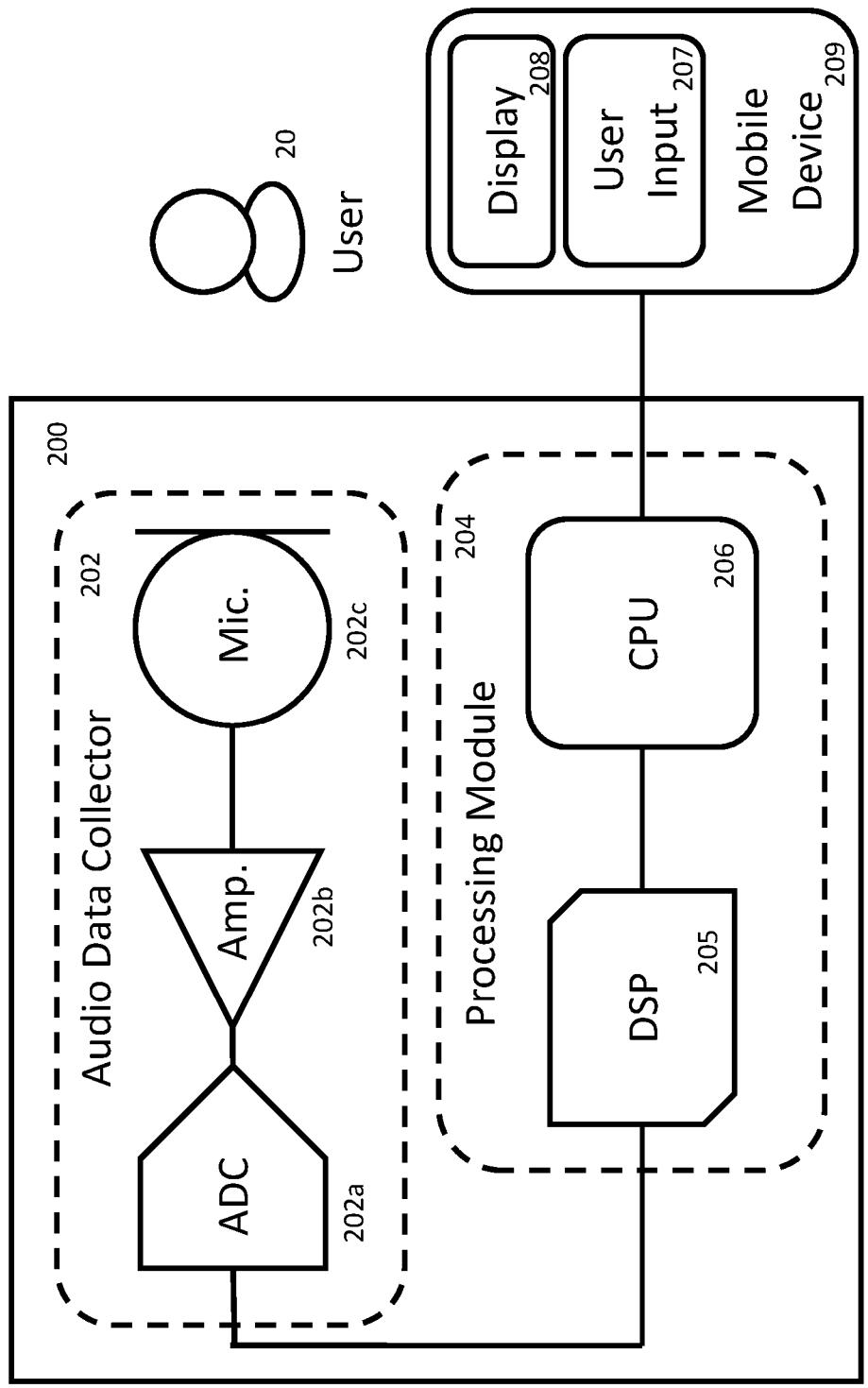
FIG. 2 depicts a system for activating personal assistance services according to another embodiment of the present inventions.

The audio data collector 202 can be embodied with a microphone module, as shown in FIG. 2. According to an embodiment of the present invention, the audio data collector 202 includes a microphone 202c for converting an acoustic energy into a voltage signal. The audio data collector 202 also includes an operational amplifier 202b coupled to the microphone for amplifying the voltage signal. And the audio data collector 202 includes an analog-to-digital converter 202a for converting the voltage signal into digital data.

Also shown in FIG. 2, is an embodiment of the processing module 204. According to an embodiment of the present invention, the processing module 204 includes a digital signal processor 205. The digital signal processor can be coupled to the audio data collector 202 to extract the plurality of acoustic features from the sample of speech. In other words, when the digital signal processor 205 executes a stored instruction set, it performs the functions of the audio feature extractor 105 (see FIG. 1). The processing module also includes a general-purpose processor 206. The general-purpose digital processing can be coupled to an output of the digital signal processor 205 (see audio feature extractor 105 in FIG. 1) to receive the plurality of acoustic features and classifies the sample of speech to a predetermined status of the user. In other words, when the general-purpose processor 206 executes a stored instruction set, it performs the functions of the classification unit 106 and the functions of the service activator 109 (see FIG. 1).

Figure 3:
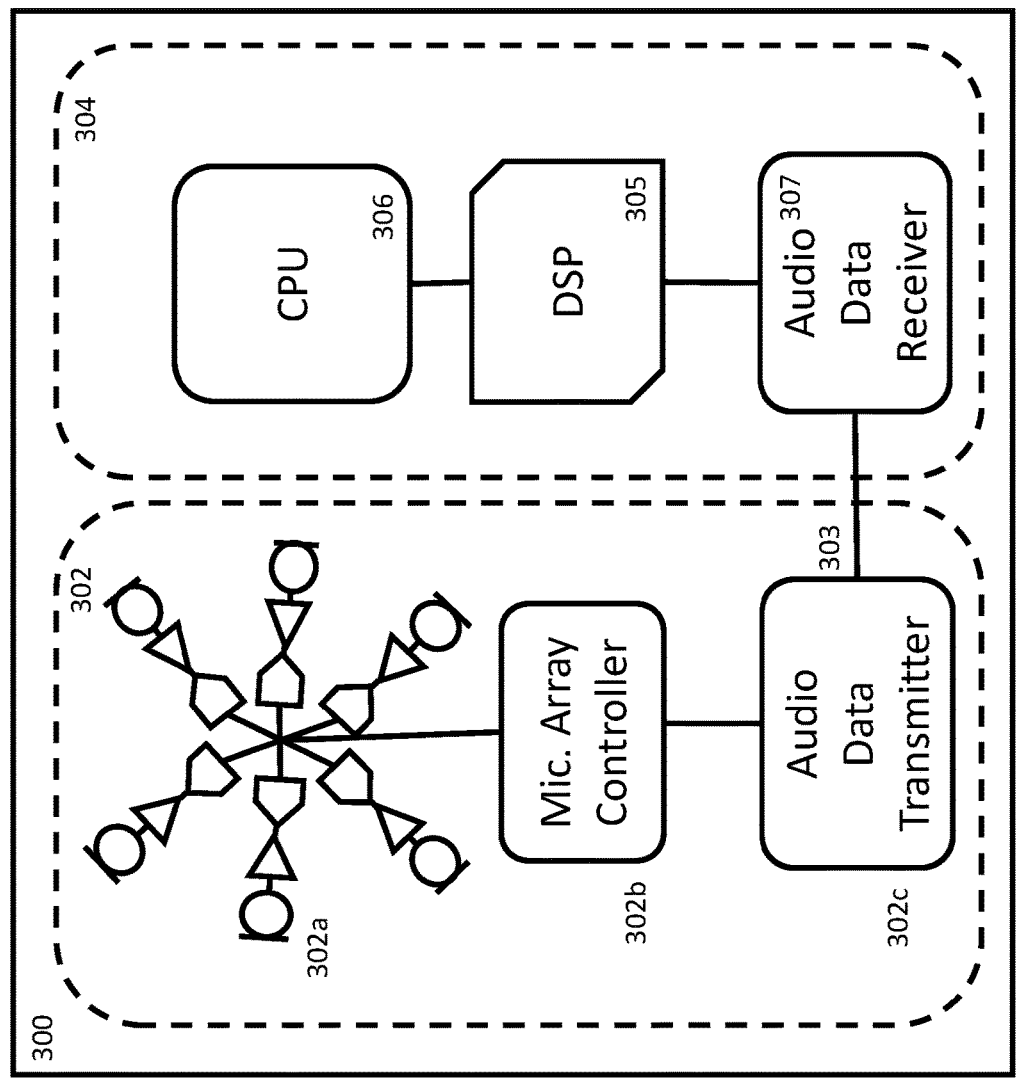
FIG. 3 a system for activating personal assistance services according to another embodiment of the present inventions.

FIG. 3 shows another embodiment of the system 300 for classifying a status of the user. As shown in FIG. 3, the audio data collector 302 can include a plurality of audio signal capture units 302a. This is commonly referred to as an array arrangement of the microphones. Each audio signal capture unit 302a includes a microphone for converting an acoustic energy into a voltage signal, an operational amplifier coupled to the microphone for amplifying the voltage signal and an analog-to-digital converter for converting the voltage signal into digital data. The audio data collector 302 also includes a microphone array controller 302b, which can be adapted to select audio data captured from one or more of the audio signal capture unites 302a. The microphone array controller 302b can also provide the selected audio data to an audio data transmitter 302c. The audio data transmitter 302c can be transmit the digital data across a communication link 303 to the processing module 304. As such, the processing module 304 and the audio data collector 302 can be coupled to communicate across any of a communication bus on a physical device, an internet protocol network, and wireless networks such as a Bluetooth network.

As shown in FIG. 3, the processing module 304 can include audio data receiver 307 for receiving digital data from the audio data transmitter 302c. As shown, the audio data receiver 307 can be coupled to an input of the digital signal processor 305 to provide the digital data for audio feature extraction.

FIG. 4A shows a method 400 for classifying a user state or status according to an embodiment of the present inventions. The method includes the step of providing an audio data collector to collect a sample of speech 402, extracting a plurality of acoustic features from the sample of speech 404, and classifying a status of the user from the plurality of acoustic features 406. the plurality of acoustic features extracted includes two or more of feature types including a time domain descriptor, a spectral domain descriptor; and a perceptual model descriptor. The plurality of acoustic features can further include the plurality of acoustic features further comprises one of an autocorrelation a descriptor, a cross-correlation between two descriptors, and a coding coefficient of a descriptor.

According to one embodiment of the method 400, the classified user status can be an emotional or affective state of the user, or the status can be a physiological state, along with a probability of the classification. As such, if the probability is determined to exceed a predetermined threshold (YES in FIG. 4), in step 408, a service is activated and is provided to a user at step 410. According to another embodiment, if the probability of the classification is determined to not have exceed the predetermined threshold (NO in FIG. 4), the method 400 returns to step 402 to capture another speech sample.

Figure 4B:
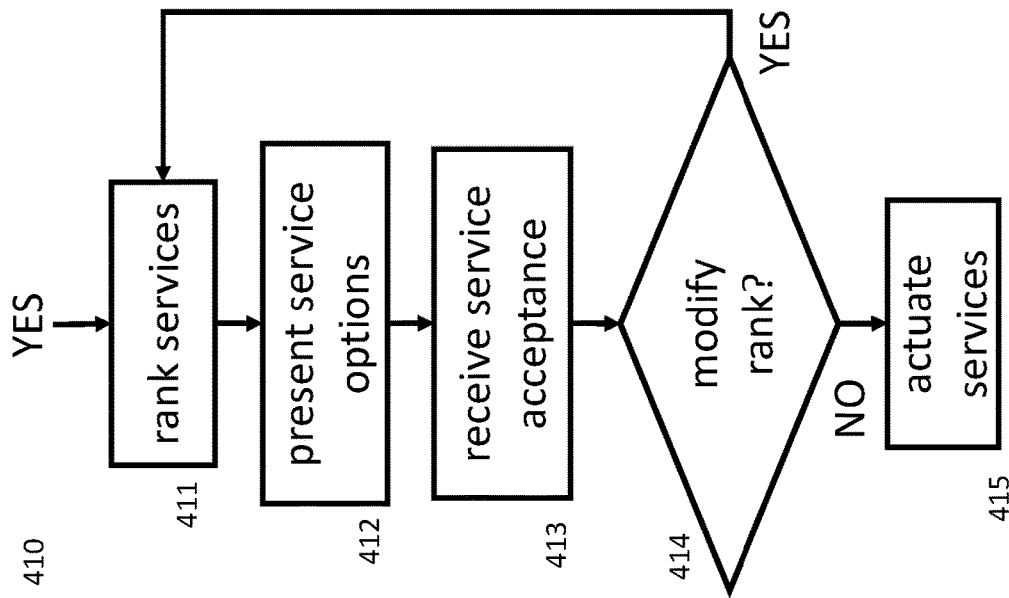

Next, FIG. 4B shows a more detailed embodiment of the activation step 410 in FIG. 4A. As shown in FIG. 4B, embodiments of the present invention provide additional steps that determines, based on a classified user state, an area of service offered by the intelligent automated assistant, and activates a health-related service to the user. In particular, in step 411, a plurality of predetermined services is ranked and stored. Further, in step 412, a ranked list or a highest ranked service is presented to the user. After receiving a user acceptance or selection of the presented service in step 413, in step 414, the method according to embodiments determines if the presented service is to be modified according to the user input. If it is determined that the presented service does not require modification, the service is activated for the user in step 415. Alternatively, if it is determined that the ranked list of services or the highest ranked service is to be modified or changed, the method returns to step 411 and repeats the ranking of the services.

Figure 4C:
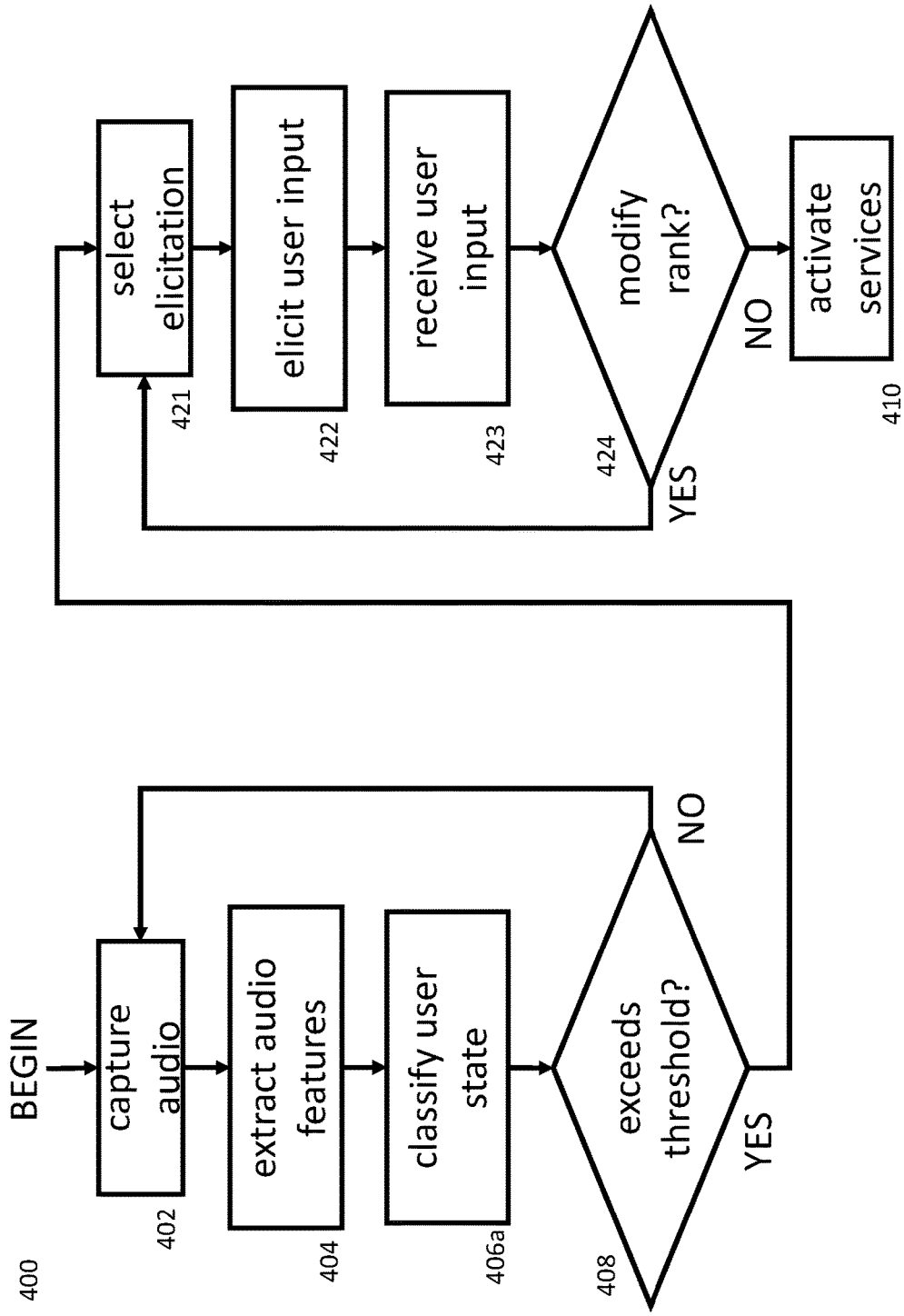

According to other embodiments, as shown in FIG. 4C, steps 421, 422, 423, and 424 are includes between previously described steps 408 and 410. In particular, a user input elicitation is selected in step 421. A user input elicitation can be provided through a text-to-voice interface or conventional user interfaces. In step 422, the user elicitation is presented to the user in order to collect the intended user input. After the user input is received in step 423, in step 424, the method determines whether the list of ranked services is changed.

In case of MDD, a ranked list of services can include, in case of a low risk status, 1) providing digital educational material, 2) providing care provider resources and referrals; 3) providing connections to support networks; in case of a medium risk status, 1) digital cognitive behavioral therapy, 2) a referral to clinical care, 3) a referral to a psychologist, psychiatrist, social worker, or counselor, 4) a recommendation to over the counter SSRI; and in case of a high risk status, 1) a recommendation and direct referral to clinical intervention.

According to an embodiment of the present invention, in step 406, a decision tree based method is implemented to perform the classification. An embodiment of the decision tree is described with respect to FIGS. 5A-C below.

In other embodiments, the classification can be performed with other established statistical algorithms and methods well-known in the art, useful as models or useful in designing predictive models, can include but are not limited to: analysis of variants (ANOVA); Bayesian networks; boosting and Ada-boosting; bootstrap aggregating (or bagging) algorithms; decision trees classification techniques, such as Classification and Regression Trees (CART), boosted CART, Random Forest (RF), Recursive Partitioning Trees (RPART), and others; Curds and Whey (CW); Curds and Whey-Lasso; dimension reduction methods, such as principal component analysis (PCA) and factor rotation or factor analysis; discriminant analysis, including Linear Discriminant Analysis (LDA), Eigengene Linear Discriminant Analysis (ELDA), and quadratic discriminant analysis; Discriminant Function Analysis (DFA); factor rotation or factor analysis; genetic algorithms; Hidden Markov Models; kernel based machine algorithms such as kernel density estimation, kernel partial least squares algorithms, kernel matching pursuit algorithms, kernel Fisher's discriminate analysis algorithms, and kernel principal components analysis algorithms; linear regression and generalized linear models, including or utilizing Forward Linear Stepwise Regression, Lasso (or LASSO) shrinkage and selection method, and Elastic Net regularization and selection method; glmnet (Lasso and Elastic Net-regularized generalized linear model); Logistic Regression (LogReg); meta-learner algorithms; nearest neighbor methods for classification or regression, e.g. Kth-nearest neighbor (KNN); non-linear regression or classification algorithms; neural networks; partial least square; rules based classifiers; shrunken centroids (SC): sliced inverse regression; Standard for the Exchange of Product model data, Application Interpreted Constructs (StepAIC); super principal component (SPC) regression; and, Support Vector Machines (SVM) and Recursive Support Vector Machines (RSVM), among others. Additionally, clustering algorithms as are known in the art can be useful in determining subject sub-groups.

Figure 5A:
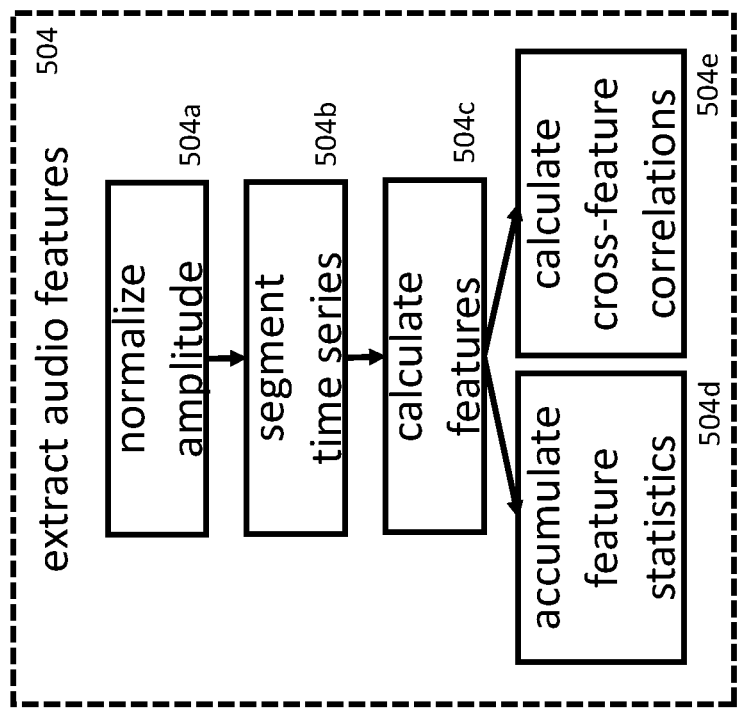

With respect to FIG. 5A, there is provided a detailed example of the step 504 for extracting a plurality of acoustic features for an embodiment of the method 400. In particular, an acoustic feature (acoustic descriptor) can be segmented from a time series of audio data (step 504b). Each acoustic feature can be defined as a feature parameter computed from a short-duration frame $x_k(n)$ having a sample length $N_{sample}$ from an audio signal at time $t=k \cdot T_{sample}$. The length of the frame can be selected to ensure substantial stationarity of the feature parameter within the frame, and to ensure that the frame contains sufficient number of samples n to compute feature parameter with statistical confidence. A typical frame lengths can vary from 10 to 35 ms.

In step 504c, a feature is calculated from a segment of the audio data. In particular, a time domain feature, a spectral or frequency domain feature, or a perceptual model feature can be calculated.

According to one embodiment, a time domain feature can be computed directly from the time domain signal $x_k(n)$, for example, the rate of zero-crossings (ZCR), amplitude statistics, and signal energy. The Zero-Crossing Rate (ZCR) describes the number of sign changes c of $x_k(n)$ per unit of time (typically one second).

$ZCR=c/1.0 \text{ s}$

A sign change can be defined as when the condition $x(n-1)x(n)<0$ is satisfied. Similarly, a sign change can be defined as when both conditions $x(n-1)x(n+1)<0$ and $x(n)=0$ are satisfied.

Amplitude statistics such as maximum and minimum signal amplitudes, or the maximum absolute value of the amplitudes can be calculated directly from $x_k(n)$.

Signal energy can be computed directly from $x_k(n)$ as well. Assuming an audio signal to have a mean value of zero, the signal energy E for a signal $x(n)$ with $n \in [0; N-1]$, is defined as the sum of squared amplitudes of the signal x, or $E = \sum_{n=0}^{N-1} x^2(n)$.

According to another embodiment, a frequency domain or spectral feature can be computed in step 504c. We can define a general spectrum $X(m)$, which can be a magnitude spectrum $X_M(m)$, a power spectrum $X_P(m)$, power spectral densities in dB, or a band or filterbank spectrum.

With a general spectrum $X(m)$, we can compute a set of frequency domain feature that satisfy a relation $f=F(m)$ and $m=F-1(f)$ between the linear frequency f in Hz and the bin index m.

Most spectral features can be computed from a sub-band range defined by the lower and upper bin indices $m_{lower}$ and $m_{upper}$, i.e. the spectrum spanning the range between $m_{lower}=1$ and $m_{upper}=M$. For a case of constrained sub-band frequency range with lower and upper border frequencies of $f_{lower}$ and $f_{upper}$, the respective integer valued bin indices are $m_{lower}=\lfloor F-1(f_{lower})+0.5\rfloor$ and $m_{upper}=\lfloor F-1(f_{upper})+0.5\rfloor$.

Various conventional spectral features can be computed. For example, band energy, spectral slope, flatness, centroid, moments, entropy, and differences can be computed per conventional definitions within the sub-band range as defined above.

Furthermore, a short-duration autocorrelation measure can be calculated within a frame. The short-time Autocorrelation function (ACF) can provide a high resolution for low frequency periodicities within a frame–the autocorrelation provides a measure of the signal's self-similarity at discrete time lags $\tau \in [-\tau_{max}, \tau_{max}]$.

Furthermore, a Cepstrum can be computed. The Cepstrum can be computed by combining a Fourier transform, its inverse and the natural logarithm function:

$$\text{Cepstrum}=FFT-1[\ln(FFT(x) \cdot FFT^*(x))]=FFT-1[\ln(|FFT(x)|2)]$$

The effect of the natural logarithm is a temporal separation of the source and filter parts of the audio signal x in the Cepstrum.

Pitch of the audio signal can be computed. The estimation of pitch can be approximated by an estimation of the fundamental frequency F0. Where pitch is a perceptual term which refers to the perceived tonality, i.e. by a human listener. Pitch is related to the F0, i.e., the lowest frequency in the harmonic series of the tone. An F0 estimation can be computed by conventional techniques, for example by the RAPT algorithm from David Talkin.

Furthermore, formants or the resonance frequencies of the vocal tract system can be computed, which characterize phonemes such as voiced vowels. They are visible in speech spectra as maxima of the envelope. From this, one method for calculation of formants is by applying a peak-picking algorithm directly to speech power spectra.

Furthermore, a parametrization in the form of Line Spectral Pairs (LSPs) can be computed by conventional techniques. The LSPs are related to the formants of the speech signal, which are estimated from the roots of the polynomial H(z). Precisely, two LSFs enclose a formant as left and right boundaries.

Next, with respect to FIGS. 5B and 5C, there is provide an example implementation of the classifying step 506. The classification function can be provided by either an online or an offline trained classifier. As an illustrative example, FIG. 5B and the following paragraphs provide a procedure to construct an off-line trained classifier.

With respect to FIG. 5B and the step of select features 507a, many common feature selection methodologies can be implemented. In general, the feature selection method is chosen 1) to uncover and account for nonlinear interactions between the features, and 2) to reduce an overfit to data.

Deprioritized by the first consideration are methods based on linear classification models, for example, LASSO. At the same time, the nonlinear interactions between the features can be addressed by tree-based feature selection methods. However, because methods based on individual trees are known to be unstable to minor changes in the data and prone to overfitting, we used a tree-based ensemble approach, Random Forests (RF), for feature selection.

RF consists of a plurality of decision trees. Every node in the decision tree is a condition on a single feature, designed to divide the dataset into two subsets such that similar response values end up in the same subset. The measure based on which the locally optimal splitting condition is chosen is called the Gini impurity. When training a decision tree, it is computed how much each feature decreases the weighted impurity in the tree. For a forest, the impurity decrease from each feature can be averaged and the features are ranked according to this measure.

Generally, we select a small number of the top-ranked features to include in the final classification model. Deciding how many features to select. To help determine this cut-off, and thereby which features to select, we introduce a large number of random features, which are independent of the target variable, i.e. the user status class, and include them among the speech features. Then, only features having importance greater than that of all the random features are selected. This typically results in only a handful of features being selected (on the order of 10-20, depending on the size of the training set, etc.).

According to one embodiment, the following settings for the step of select features 507a: 1) number of trees: 5000, 2) minimum number of cases (individual subjects) at a node: 5, which is the default: 10, 3) number of random features: 100.

With these parameter settings for the step of select features 507a, we have found this to be a sufficient number of random features to provide a feature importance score threshold.

Next, with respect to FIG. 5B, there is provide an example implementation to the method steps to (off-line) train a classifier according to an embodiment of the present invention.

User state classification can be trained based on an individual's response to health surveys, for example, the PHQ-9 questionnaire.

In a typical study population, the predetermined user state or status may be found in a small minority of the population. This imbalance of classes poses a problem for most standard classification approaches, which seek to minimize overall misclassification cost and, thereby, tend to be biased towards proper classification of the majority class (i.e. standard methods have difficulty predicting the minority class when the data is highly skewed). It is important to achieve high accuracy in predicting both classes.

Conventional methods for imbalanced classification tasks. For example, boosting algorithms can be implemented to build an ensemble of weak classifiers iteratively. During each iteration, example weights are modified with the goal of correctly classifying examples in the next iteration, which were incorrectly classified during the current iteration. All models that are constructed during the boosting process participate in a weighted vote to classify unlabeled examples. This is effective for dealing with class imbalance because the minority class examples are most likely to be misclassified and therefore given higher weights in subsequent iterations. The method we have used accomplishes boosting by resampling, in which the training data is re-sampled according to examples' assigned weights. This resampled data set is used to construct the model for the given iteration.

Data sampling is another common approach used to address class imbalance in classification tasks. This approach balances the classes in the training data by either undersampling (removing examples from the majority class) or by oversampling (adding examples to the minority class). The goal in either case is to is to present the learning algorithm to be used with an equal number of positive and negative classes. Many sampling methods have been proposed in the literature. The simplest such method is random re-sampling. Random oversampling duplicates examples in the minority class until class balance is attained, while random undersampling removes examples from the majority class to achieve class balance.

While undersampling results in a loss of information by deleting examples from the training class, the benefit can be a reduced computational time for model training. No information is lost via oversampling, but the price is increased computational cost. In many cases, little or no predictive accuracy is lost via undersampling and often undersampling performs better than oversampling, so it is preferable to oversampling when computational costs are a consideration.

According to an embodiment of the present invention, a boosting method dealing with imbalanced classes, RUSBoost is selected as the method to train the user state classifier in step 507. This combines random undersampling (RUS) of the majority class with boosting (boost). The boosting algorithm it uses is AdaBoost, and the weak learners used in each iteration are classification trees.

What is claimed is:

1. A system for activating personal assistance services to a user, the system comprising:
   a processing module comprising an audio feature extractor, a service activator, and a classification unit;
   said service activator adapted to activate said system based on contextual health data derived from non-linguistic content of a speech sample;
   said audio data collector adapted to collect said sample of speech;
   said audio feature extractor adapted to extract a plurality of acoustic features from the sample of speech, wherein said plurality of acoustic features extracted comprise:
      an auto-correlated feature;
      a feature resulting from cross-correlation between two or more of said extracted acoustic features; and
      a coding coefficient of a feature;
   said classification unit adapted to classify one or more of a plurality of health states of the user by using a combination of the extracted plurality of acoustic features and the contextual health data received from a contextual data collector coupled to the system, wherein a combination of Random Forest and Gini Impurity is used to rank the extracted plurality of acoustic features before combining the extracted plurality of acoustic features with the contextual health data for said classification of said health state of said user; and
   said service activator adapted to present a ranked list of services to the user based on the health state of the user as classified by the classification unit.

2. The system of claim 1, wherein the system is further coupled to a display unit adapted to display a service activation confirmation to the user.

3. The system of claim 1, wherein the audio data collector comprises:
   a microphone adapted to convert an acoustic energy into a voltage signal;
   an operational amplifier coupled to the microphone adapted to amplify the voltage signal; and
   an analog-to-digital converter adapted to convert the voltage signal into digital data.

4. The system of claim 1, wherein the audio data collector comprises:
   a plurality of audio signal capture units, wherein each audio signal capture unit comprises:
      a microphone adapted to convert an acoustic energy into a voltage signal;
      an operational amplifier coupled to the microphone adapted to amplify the voltage signal; and
      an analog-to-digital converter adapted to convert the voltage signal into digital data;
   a microphone array controller adapted to select the digital data captured from one or more of said audio signal capture units, and provide the selected digital data to an audio data transmitter; and
   said audio data transmitter adapted to transmit the digital data across a communication link to the processing module.

5. The system of claim 1, wherein the audio feature extractor comprises a digital signal processor, wherein the digital signal processor is coupled to the audio data collector for said extraction of the plurality of acoustic features from the sample of speech, wherein the classification unit comprises a processor, and wherein the processor is coupled to an output of the audio feature extractor to receive the plurality of acoustic features extracted by the digital signal processor of the audio feature extractor.

6. The system of claim 1, wherein the plurality of acoustic features extracted by the audio feature extractor further comprises two or more feature types, wherein said feature types comprise:
   a time domain feature;
   a spectral domain feature; and
   a perceptual model descriptor feature.

7. The system of claim 1, further comprising:
   said classification unit determining a sequence of traversal through an acyclic graph of the acoustic features, in accordance with a statistical distribution of the acoustic features;
   said classification unit traversing the acyclic graph by detecting a threshold crossing for each node of the acyclic graph; and
   said classification unit providing an output, wherein the output is predictive of a health state of the user.

8. A method of activating personal assistance services to a user, the method comprising:
   providing a system comprising an audio data collector and a processing module, wherein said processing module comprises an audio feature extractor, a service activator, and a classification unit;
   activating said system, by said service activator, based on contextual health data derived from non-linguistic content of a speech sample;
   collecting said sample of speech from a microphone, by said audio collector;
   extracting a plurality of acoustic features from the collected sample of speech, by an audio feature extractor of said processor module, wherein said plurality of acoustic features extracted comprise:
      an auto-correlated feature;
      a feature resulting from cross-correlation between two or more of said extracted acoustic features; and
      a coding coefficient of a feature;
   classifying one or more of a plurality of health states of the user by using the extracted plurality of acoustic features and the contextual health data received from a contextual data collector coupled to the system, by a classification unit of the processor module, wherein a combination of Random Forest and Gini Impurity is used to rank the extracted plurality of acoustic features before combining the extracted plurality of acoustic features with the contextual health data for said classification of the health state of the user; and activating a personal assistance service, by said service actuator, to present a ranked list of services to the user based on the health state of the user as classified by the classification unit, wherein said service activator uses the non-linguistic content of the speech sample to activate the system.

9. The method of claim 8, further comprising coupling a display unit to the system for displaying a service activation confirmation to the user.

10. The method of claim 8, further comprising:
converting an acoustic energy into a voltage signal, by a microphone of the audio data collector;
amplifying the voltage signal, by an operational amplifier of the audio data collector, wherein the operational amplifier is coupled to the microphone; and
converting the voltage signal into digital data, by an analog-to-digital converter of the audio data collector, wherein the analog-to-digital converter is coupled to the operational amplifier.

11. The method of claim 8, further comprising:
providing a plurality of audio signal capture units, wherein each audio signal capture unit performs the steps comprising:
converting an acoustic energy into a voltage signal, by a microphone of the audio data collector;
amplifying the voltage signal, by an operational amplifier coupled to the microphone; and
converting the voltage signal into digital data, by an analog-to-digital converter coupled to the operational amplifier.

12. The method of claim 8, further comprising:
providing a digital signal processor within said processor module for said extraction of said plurality of acoustic features from the sample of speech; and
receiving the plurality of acoustic features extracted by the digital signal processor, by the classification unit of the processor module.

13. The method of claim 8, wherein the plurality of acoustic features comprises two or more feature types, wherein said feature types comprise:
a time domain feature;
a spectral domain feature; and
a perceptual model feature.

14. The method of claim 8, further comprising:
determining, in accordance with a statistical distribution of the acoustic features, a sequence of traversal through an acyclic graph of the acoustic features, by the classification unit;
traversing the acyclic graph by detecting a threshold crossing for each node of the acyclic graph, by the classification unit;
providing an output, by the classification unit, wherein the output is the health state of the user.

15. A mental and physical health context aware intelligent automated assistant, comprising:
a processor and a memory for storing instructions executable by said processor;
an audio data collector, a classification unit and a service activator;
said processor further configured to use said service activator to activate said mental and physical health context aware intelligent automated assistant based on non-linguistic features of audio input received from a user;

said processor configured to receive a user request through said audio data collector, wherein the user request including a speech or other includes said audio input received from a user;
said processor further configured to receive contextual health data from a contextual data collector coupled to said mental and physical health context aware intelligent automated assistant, wherein said processor derives said non-linguistic features of the audio input from said received contextual health data;
said processor further configured to classify a mental or physical health state of the user from a plurality of predetermined health domains, using said classification unit, wherein said classification is performed using said derived non-linguistic features of the audio input;
said processor further configured to rank, based on said classification, a list of services to be offered to the user by the mental and physical health context aware intelligent automated assistant; and
said processor further configured to provide a health-related service to the user from said ranked list of services based on a ranking order.

16. The mental and physical health context aware intelligent automated assistant of claim 15, further comprising:
an user interface for eliciting an input from the user by providing a feedback to the user; and
receiving the user input through said user interface to determine one or more health parameters associated with the predetermined health domains.

17. The mental and physical health context aware intelligent automated assistant of claim 16, wherein in the step of eliciting further comprises:
offering service suggestions based on predetermined parameters associated with the predetermined health domains.

18. The mental and physical health context aware intelligent automated assistant of claim 15, wherein the classified health state of the user is shared with one or more other users or health care providers.

19. The mental and physical health context aware intelligent automated assistant of claim 15, wherein an appointment is scheduled with a health care provider based on the classified health state.

20. The system of claim 4, wherein the processor module further comprises an audio data receiver adapted to receive the digital data from the audio data transmitter, wherein the audio feature extractor further comprises a digital signal processor coupled to an output of the audio data receiver, wherein the digital signal processor is configured to extract the plurality of acoustic features from the sample of speech, wherein the classification unit comprises a processor coupled to an output of the digital signal processor, and wherein the processor is configured to receive the plurality of acoustic features from the digital signal processor.

21. The method of claim 11, wherein an audio data receiver in the processor module receives the digital data from the audio data transmitter, wherein a digital signal processor in the processor module coupled to an output of the audio data receiver extracts the plurality of acoustic features from the sample of speech, and wherein a processor in the processor module coupled to an output of the digital signal processor receives the plurality of acoustic features from the digital signal processor.

* * * * *